United States Patent [19]
Goldstein et al.

[11] Patent Number: 5,221,743
[45] Date of Patent: Jun. 22, 1993

[54] PROCESS FOR PRODUCING ISOCYANURATES BY CYCLOTRIMERIZING ISOCYANATES USING POLYMER-BOUND CATALYSTS

[75] Inventors: Stephen L. Goldstein; Curtis P. Smith, both of Cheshire, Conn.

[73] Assignee: Olin Corporation, Cheshire, Conn.

[21] Appl. No.: 844,265

[22] Filed: Mar. 2, 1992

[51] Int. Cl.$^5$ ............... C07D 251/32; C07D 251/34; C08G 18/16; C08G 18/80

[52] U.S. Cl. .................. 544/193; 521/107; 521/108; 521/902; 524/101; 525/330.5; 528/45; 528/48; 528/49; 528/51; 528/65; 528/67; 528/69; 528/73; 528/85; 544/221; 544/222

[58] Field of Search ............... 544/193, 221, 222; 528/49, 65, 85, 45, 51, 48, 73, 67, 68; 521/107, 108, 902; 525/330.5; 524/101

[56] References Cited

U.S. PATENT DOCUMENTS

| | | | |
|---|---|---|---|
| 3,645,979 | 2/1972 | Liebsch et al. | 544/193 X |
| 4,040,992 | 8/1977 | Bechara et al. | 544/193 X |
| 4,145,544 | 3/1979 | Kuehu | 544/193 X |
| 4,220,728 | 9/1980 | Kresta et al. | 521/121 |
| 4,265,798 | 5/1981 | Mishra | 260/32.4 |
| 4,324,879 | 4/1982 | Bock et al. | 544/193 X |
| 4,359,550 | 11/1982 | Narayan et al. | 544/193 X |
| 4,379,905 | 4/1983 | Stemmler et al. | 544/193 X |
| 4,382,125 | 5/1983 | Narayan et al. | 544/193 X |
| 4,412,073 | 10/1983 | Robin | 544/193 |
| 4,499,253 | 2/1985 | Kerimis et al. | 544/193 X |
| 4,537,961 | 8/1985 | Robin | 544/193 |
| 4,582,888 | 4/1986 | Kase et al. | 544/193 X |

*Primary Examiner*—Floyd D. Higel
*Attorney, Agent, or Firm*—Dale Lynn Carlson

[57] ABSTRACT

This invention relates to a process for preparing a trimer by the steps of: (a) cyclotrimerizing a polyisocyanate in the presence a polymer-bound trimerization catalyst by contacting said polyisocyanate with said catalyst at a temperature of between about 20° and about 135° C. in a reaction to form an isocyanurate-containing cyclotrimerized isocyanate wherein a portion of the isocyanate moieties comprising said polyisocyanate are converted to isocyanurate groups, and (b) separating said catalyst from said cyclotrimerized isocyanate in order to stop said reaction after a desired amount of isocyanate moieties in said polyisocyanate have been converted to isocyanurate moieties.

18 Claims, No Drawings

PROCESS FOR PRODUCING ISOCYANURATES BY CYCLOTRIMERIZING ISOCYANATES USING POLYMER-BOUND CATALYSTS

FIELD OF THE INVENTION

This invention relates generally to isocyanurate adducts, and, more specifically, to a process for preparing isocyanate trimers using a polymer-bound catalyst.

BACKGROUND OF THE INVENTION

Polyisocyanurate adducts of polyisocyanates are well-known intermediates used in the preparation of high performance urethane coatings, paints, and films. These adducts provide improved physical properties when used in such applications, as compared to difunctional isocyanates such as toluene diisocyanate. In addition, these adducts provide reduced volatility and an associated reduced toxicity hazard during use, as compared to toluene diisocyanate.

Processes for preparing these adducts are well known. Examples illustrative of these processes can be found in U.S. Pat. Nos.: 4,220,728; 4,265,798; 4,324,879; and 4,412,073. Generally, the prior art processes involve adding a catalyst which promotes the isocyanate to isocyanurate (also known as "trimerization") reaction to the precursor isocyanate, optionally in the presence, but usually in the absence, of a solvent, allowing the reaction to proceed to the desired extent and then stopping the reaction with a suitable quenching agent which destroys the activity of the catalyst.

After the residual, unreacted precursor isocyanate is removed, the resulting material, in the case where the precursor isocyanate is a diisocyanate, is a mixture of oligomers composed of 3, 5, 7, etc. precursor diisocyanate molecules joined by 1, 2, 3, etc. isocyanurate rings. Usually, this mixture is simply called "trimer".

In the case where the precursor isocyanate is polyisocyanate, the reaction is generally stopped well before all the isocyanate groups have been converted to isocyanurate groups because, otherwise, the resulting product would be an unusable polymer having a very high (theoretically infinite) molecular weight and viscosity. However, the cost of equipment and energy to remove residual, unreacted precursor isocyanate dictate that the reaction not be stopped too soon. Generally, the reaction is run to more than 10% conversion but less than 50% conversion. The preferred range is between 20 and 35%. The reaction is typically stopped using a quenching agent. The reaction between conventional trimerization catalysts and quenching agents typically results in the formation of an insoluble product which is typically removed by filtration using a filter aid.

Unfortunately, both the quenching agent and the filter aid increase the likelihood of introducing undesirable impurities into the product. Accordingly, new processes for producing trimers that do not employ a quenching agent and filter aid(s), and employ fewer process steps than prior art processes, would be highly desired by the trimer manufacturing community. Heretofore, such processes have not been known to the knowledge of the present inventors.

SUMMARY OF THE INVENTION

In one aspect, the present invention relates to a process for preparing a trimer by cyclotrimerizing an isocyanate in the presence a polymer-bound trimerization catalyst to form an isocyanurate-containing cyclotrimerized isocyanate.

In another aspect, the present invention relates to a process for preparing a trimer by the steps of:
(a) cyclotrimerizing a polyisocyanate in the presence a polymer-bound trimerization catalyst by contacting said polyisocyanate with said catalyst at a temperature of between about 20° and about 150° C., preferably between about 20° and about 135° C., in a reaction to form an isocyanurate-containing cyclotrimerized isocyanate wherein a portion of the isocyanate moieties comprising said polyisocyanate are converted to isocyanurate groups, and
(b) separating said catalyst from said cyclotrimerized isocyanate in order to stop said reaction after a desired amount of isocyanate moieties in said polyisocyanate have been converted to isocyanurate moieties.

In yet another aspect, the present invention relates to a process for preparing a trimer by cyclotrimerizing an isocyanate in the presence a polymer-bound trimerization catalyst to form an isocyanurate-containing cyclotrimerized isocyanate wherein the polymer-bound trimerization catalyst consists essentially of a polymer having an alkyene group-containing polymer backbone and having trimerization catalyst moieties chemically bound to said polymer, said catalyst moieties being selected from the group consisting of: aliphatic tertiary amines; aliphatic quaternary ammonium hydroxides and fluorides; quaternary ammonium, alkali and alkali metal salts of carboxylic acids and alcohols; organo-silyl amines; organo-phosphorous and organo-arsenic compounds; and combinations thereof.

These and other aspects will become apparent upon reading the following detailed description of the invention.

DETAILED DESCRIPTION OF THE INVENTION

In accordance with the present invention, it has now been surprisingly discovered that polymer-bound trimerization catalysts are suitably prepared which are then employed in a straightforward fashion to provide a facile trimerization reaction. The term "polymer-bound" as used herein is intended to designate polymer supported trimerization catalysts which are insoluble in the trimerization reaction medium by virtue of the polymer support, and thus are easily separated from the reaction medium by removal of the polymer bound catalyst from the reaction medium after the trimerization reaction has proceeded to the desired extent of completion.

The catalyst composition useful in the process of the present invention comprises a polymer which is insoluble in the reaction medium and which contains sites that promote the trimerization reaction which are bound to the polymer through ionic or, preferably, covalent bonds. Compounds which promote the reaction converting isocyanate to isocyanurate are well known in the art. However, heretofore it was not known to the knowledge of the present inventors whether or not these various reaction promoters would still be active trimerization catalysts when bound to a polymer to provide a polymer-bound catalyst.

In accordance with the present invention, it has now been found that specific classes of functional groups are suitably employed as polymer-bound catalysts for the desired trimerization reaction. Useful moieties thus include polymer bound derivatives of the following: aliphatic tertiary amines; aliphatic quaternary ammonium hydroxides and fluorides; quaternary ammonium, alkali and alkali metal salts of carboxylic acids and alcohols; organo-silyl amines, organo-phosphorous and organo-arsenic sites; and the like. Nitrogen containing and arsine oxide containing functional groups are preferred because of their enhanced stability in the reaction medium. Tertiary amines are most preferred due to the additional advantage of their ease of regeneration, although the arsine oxide and the quaternary ammonium hydroxide functional groups are also desirable due to their excellent catalytic activity.

The polymer support for the catalyst should be inert in the trimerization medium. Additional factors to be considered in selecting preferred polymer supports are: availability; cost; stability; ease of functionalization; and, ability to be swollen and/or "wet" by the precursor isocyanate. This last characteristic is desired in order to facilitate intimate contact between the precursor isocyanate and the active sites on the polymer and then allow the resulting isocyanurate to migrate away from the catalytic site, making it available for further reaction. Because of their stability to elevated temperatures and the reaction environment, polymer backbones consisting essentially of carbon to carbon bonds, derived from alkenes, are desired, such as: ethylene, propylene, isoprene, styrene, acrylates, methacrylates, and the like. Polystyrenes are most preferred because of their thermal and chemical stability and the ease with which they can be functionalized. Preferred styrene polymers are poly(styrene co-vinylbenzylchloride), which are commercially available as so-called Merrifield resins.

The macroscopic form of the polymers that can be employed in the process of this invention can be varied significantly, including solid and/or liquid form. For example, polymers that, by virtue of their low molecular weight, for example, are soluble in the trimerization reaction medium, can be precipitated and then filtered from the reaction medium by the addition of an appropriate non-solvent for the polymer when the desired degree of trimer conversion is reached. However, recovering this non-solvent can entail additional costs. A preferred approach is to use a polymer which is "essentially insoluble" (i.e., not soluble to any substantial degree) in the trimerization reaction medium. The polymer can be utilized in the form of beads or powder or other relatively small particles. However, using the polymer in the form of small beads is generally preferred since this simplifies removal of the polymer bound catalyst through filtration and similar such techniques.

The solubility of the polymer in the trimerization reaction medium is generally inversely proportional to its crosslink density. In the case where the polymer bound catalyst is based on polystyrene, the amount of crosslinkinq is determined by the amount of divinyl benzene co-monomer used in the preparation of the polymer. In addition to effecting the solubility of the polymer bound catalyst, the crosslink density of the polymer is an important consideration because it positively affects mechanical stability while having a negative impact on the degree of swelling and/or wettability of the polymer. Crosslink densities greater than or equal to 1% and less then 10% are preferred. Those between 1 and 5% are most preferred.

It is also possible to adjust the number of catalytically active sites (i.e., functional groups) bound to the polymer. From a practical standpoint, the minimum required number of active sites on the catalyst is that amount that provides a "catalytically effective amount", i.e., an amount sufficient to catalyze the trimerization reaction. The upper limit is, in one sense, defined by the composition of the catalyst and the polymer to which it is being bound. This maximum is in practice determined by the amount that provides a catalyst that permits some control over the desired trimerization reaction. Additionally, the active site content of the polymer bound catalyst which provides a practically useful catalyst is also a function of the activity of the catalyst that is bound to the polymer. Generally, it is found that for the types of catalytic species described above, the range of 0.01 to 10 meq of catalytic sites per gram of polymer is preferred, with levels of 0.5 to 5 meq per gram being most preferred.

When the polymer bound catalyst is used in the form where it remains as a separate phase, i.e., where it is insoluble in the reaction medium, there are at least two options with respect to the manner in which the precursor isocyanate, optionally in the presence of a solvent, can be contacted with the catalyst, either (a) packed in a cartridge or tube, or (b) dispersed in a stirred reactor. In either case, the system can be operated in batches, e.g., where the system is charged with isocyanate, the reaction is typically run until the desired level of conversion is reached, and then the product is separated from the catalyst by filtration or similar such means. Alternatively, the system can be run as a continuous process wherein isocyanate is continuously added to the system while the product trimer having the desired level of conversion is continuously withdrawn. Potential hardware configurations include: a Continuously Stirred Tank Reactor ("CSTR") with the catalyst dispersed in the isocyanate; a CSTR which serves as a reservoir for the isocyanate/trimer mixture that is repetitively passed, in parallel, through a battery of catalyst packed cartridges, wherein relatively low levels of conversion are achieved in each pass; or a catalyst packed tube, wherein the desired level of conversion is reached in a single pass through the tube.

A range of polymer bound catalyst concentrations may be used in the process of this invention. The factors to be considered in the selection of preferred catalyst concentrations are: the activity of the catalyst being used; the degree of conversion desired; and, the temperature at which the reaction is conducted. Generally, levels between 0.01 and 10 parts of polymer bound catalyst per 100 parts of precursor isocyanate are preferred. Levels between 0.05 and 2 parts of catalyst per 100 parts of precursor isocyanate are most preferred.

Co-catalysts are optionally and desirably employed in the process of the present invention as a source of active hydrogens for the isocyanurate formation reactions. These co-catalysts can be also envisioned as co-reactants since they are typically incorporated into the trimer product. Thus, the co-catalysts unfortunately tend to reduce the purity of the trimer product, and therefore in a preferred aspect of the present invention the polymer bound catalysts also provide a source of active hydrogens for promoting the trimerization reaction. The co-catalysts may be any isocyanate-reactive hydrogen containing material such as amines, alcohols, carbamates, ureas and the like. The preferred co-catalysts are primary and secondary alcohols, such as, for example, methanol, ethanol, 2-propanol, 1,3-dihydroxy-2-hexyl propane, triethylene glycol monomethyl ether, and the like. Preferably, the co-catalyst is employed in an amount of between about 1:1 and about 10:1 molar equivalents based upon the amount of polymer-bound catalyst employed in the process of the present invention.

A range of temperatures may be used in the process of this invention. The factors to be considered in the selection of preferred reaction temperatures are the amount and the activity of the catalyst being used and the degree of conversion desired. Generally, somewhat elevated temperatures are preferred because they drive the reaction at a reasonable rate. Temperatures between 20° and 150° C. are preferred with temperatures between 20° and 135° C. being most preferred.

The time required for the process of this invention is dependent on the temperature, the amount and type of catalyst used and the degree of conversion sought. Generally, it is desirable that a combination of temperature, catalyst activity and catalyst concentration be used that achieves the required level of conversion within a period of 0.5 to 8 hours.

The cyclotrimerization reaction is effectively stopped by removal of the catalyst. The catalyst optionally may be deactivated prior to removal. The catalyst is deactivated by the addition of a suitable blocking agent. Such agent reacts preferentially with the catalytic sites and blocks further reaction with isocyanate functional group. Agents such as hydrogen containing acids or salts of such acids that thermally liberate the acid, alkyl halides and the like, are employed in an amount of 1:1 and about 10:1 molar equivalents based on the amount of polymer-bound catalyst employed in the process of the present invention.

Once the reaction mass has been separated from the polymer bound catalyst, most of the unreacted isocyanate monomer, and any optionally used solvent, is preferably removed from the product trimer by evaporation by any convenient means including simple distillation or thin film evaporation at elevated temperatures and atmospheric or, preferably, reduced pressure, followed by a more stringent process for removal of any remaining residual solvent and precursor isocyanate monomer. This final step is preferably accomplished using a wiped film evaporator ("WFE") in which the exposure of the product stream to high temperatures is minimized. The use of WFE is well-known in the art. Briefly, the process involves passing the monomer containing feed through the WFE apparatus at elevated temperatures, 80° to 180° C., preferably between 100° and 160° C., and reduced pressure, 0.01 to 5 mm Hg, Preferably between 0.1 and 2 mm Hg. The feed rate is dependant on the heated surface area of the apparatus, but should be slow enough to permit the removal of most of the residual diisocyanate monomer but fast enough to assure that the product is not exposed to high temperatures for an unnecessarily long period of time. At the end of this treatment, the residual monomer content should be less than 0.2%, preferably less than 0.1% by weight of the product.

The process of the present invention is suitably employed in the production of a wide range of isocyanate trimers, including hexamethylene diisocyanate ("HDI") trimer, isophorone diisocyanate ("IPDI") trimer, $H_{12}MDI$ trimer, toluene diisocyanate ("TDI") trimer, methylene diphenylene diisocyanate ("MDI") trimer, naphthalene diisocyanate ("NDI") trimer, cyclohexylene diisocyanate ("CHDI") trimer, 1,4-phenylene diisocyanate ("PPDI") trimer, bitolyene diisocyanate ("TODI") trimer, xylyene diisocyanate ("XDI") trimer, tetramethyl xylyene diisocyanate ("TMXDI") trimer, 1,3-bis(isocyanatomethyl) cyclohexane ("$H_6MDI$") trimer, and the like, as well as, mixtures thereof.

The following examples are intended to illustrate, but in no way limit the scope of, the present invention.

EXAMPLE 1

A-Preparation of a Polymer Bound Trimethyl-hydroxyethyl-ethylenediamine Derived Catalyst To 25 gm Merrifield Resin [poly(styrene-co-vinylbenzylchloride), 1 meq Cl/gm, 1% crosslink] was added 500 ml toluene and 21 gm trimethyl-hydroxyethylethylenediamine. The mixture was stirred and heated at 65° C. for 10 hours. The resin was isolated by filtration and washed several times with toluene, then several times with methanol, and then several times with water. The resin was then treated with NaOH, portionwise, until the filtrate failed to shown any precipitate when mixed with aqueous $AgNO_3/HNO_3$. The resin was washed with water until the filtrate was neutral to pH paper, then several times with methanol, and then several times with toluene. After drying for 18 hours under vacuum, 28.6 gm of a friable, tan solid was recovered.

B-Trimerization Test

To 0.72 gm of the above resin was added 104.9 gm HDI. The mixture was stirred and heated to 55°-60° C. for 90 minutes. An IR spectrum of the liquid showed that 30% of the HDI had been converted to trimer.

C-Trimerization Test—Stopping the Reaction

To 0.77 gm of the above resin was added 134.4 gm HDI. The mixture was stirred and heated to 55°-60° C. for approximately 45 minutes. At this point an IR spectrum of the liquid showed that 18% of the HDI had been converted to trimer. The mixture was filtered under nitrogen through a sintered glass filter funnel. About 100 ml of the filtrate was then heated to 55°-65° C. for 4 hr. During the heating period and at the end the IR spectra showed no increase or decrease in trimer concentration (18%).

D-Trimerization Test—Continuing the Reaction

To 0.75 gm of the above resin was added 110.4 gm HDI. The mixture was stirred and heated to 55°-60° C. for 90 minutes. An IR spectrum of the liquid showed that 30% of the HDI had been converted to trimer. Most of the supernatant liquid (97.6 gm) was decanted from the catalyst and 102.7 gm fresh HDI was added. The mixture was heated at 55°-60° C. for 90 minutes. An IR spectrum of the liquid showed that 32% of the HDI had been converted to trimer. This process of decanting the supernatant liquid, adding fresh HDI and then heating was repeated an additional two times with no apparent loss in activity of the catalyst.

EXAMPLE 2

A-Preparation of AMBERLYST A-21 ion exchange resin

A 100 gm sample of AMBERLYST(r) A-21 (an aliphatic tertiary amine bound to polystyrene, 57% water, 4.8 meq/gm amine, a product of Rohm and Haas Company) was washed several times with methanol, until the filtrate was colorless and then several times with toluene. After drying for 18 hours under vacuum, 32.5 gm of light tan colored beads were recovered.

B-Trimerization Test

To 1 gm of the above resin was added 15 gm HDI. The mixture was stirred and heated to 100° C. for 3 hours. An IR spectrum of the liquid showed that 10% of the HDI had been converted to trimer.

C-Trimerization Test with Methanol Added

To 1 gm of the above resin was added 15 gm HDI and 0.1 gm methanol. The mixture was stirred and heated at 100° C. for 3 hours. An IR spectrum of the liquid showed that more than 25% of the HDI had been converted to trimer.

EXAMPLE 3

A-Preparation of a Polymer Bound N-methylhydroxyethylamine Derived Catalyst

To 25 gm Merrifield Resin [poly(styrene-covinylbenzyl- chloride), 1 meq Cl/gm, 1% crosslink] was added 500 ml toluene and 20 gm N-methyl-hydroxyethylamine. The mixture was stirred and heated at 75° C. for 10 hours. The resin was isolated by filtration and washed several times with toluene, then several times with methanol, and then several times with water. The resin was then treated with 1N NaOH, portionwise, until the filtrate failed to show any Precipitate when mixed with aqueous $AgNO_3/HNO_3$.

The resin was washed with water until the filtrate was neutral to pH paper, then several times with methanol, and then several times with toluene. After drying for 18 hours under vacuum 28.6 gm of a friable, white solid was recovered. Elemental analysis showed that the Product was 1.3% nitrogen.

B-Trimerization Test

To 1 gm of the above resin was added 10 gm HDI. The mixture was stirred and heated to 140° C. for 9 hours. An IR spectrum of the liquid showed that 24% of the HDI had been converted to trimer.

EXAMPLE 4

A-Preparation of a Polymer Bound N,N-dimethylhydroxyethylamine Derived Catalyst

To 25 gm Merrifield Resin [poly(styrene-covinylbenzyl- chloride), 1 meq Cl/gm, 1% crosslink] was added 500 ml toluene and 25 gm N,N-dimethyl-hydroxyethylamine. The mixture was stirred and heated at 110° C. for 24 hours. The resin was isolated by filtration and washed several times with toluene, then several times with methanol, and then several times with water. The resin was then treated with 1N NaOH, portionwise, until the filtrate failed to show any precipitate when mixed with aqueous $AgNO_3/HNO_3$.

The resin was washed with water until the filtrate was neutral to PH paper, then several times with methanol, and then several times with toluene. After drying for 18 hours under vacuum, 25.1 gm of a friable, pale yellow solid was recovered.

B-Trimerization Test

To 0.103 gm of the above resin was added 15.2 gm HDI. The mixture was stirred and heated to 50°–55° C. for 2 hours. An IR spectrum of the liquid showed that 28% of the HDI had been converted to trimer.

EXAMPLE 5

A-Preparation of AMBERLYST A-27 ion exchange resin

A sample of AMBERLYST® A-27 (an aliphatic quaternary ammonium chloride bound to polystyrene, a product of Rohm and Haas Company) was washed several times with methanol, until the filtrate was colorless, then several times with toluene, then several times with methanol, and then several times with water. The resin was then treated with 1N NaOH, portionwise, until the filtrate failed to show any precipitate when mixed with aqueous $AgNO_3/HNO_3$.

The resin was washed with water until the filtrate was neutral to pH paper, then several times with methanol, and then several times with toluene. The product was dried for 18 hours under vacuum.

B-Trimerization Test

To 1 gm of the above resin was added 15 gm HDI. The mixture was stirred and slowly heated to 125° C. over a period of 6 hours. An IR spectrum of the liquid showed that 12% of the HDI had been converted to trimer.

EXAMPLE 6

A-Preparation of Poly(4-Vinyl Pyridine)

A sample of poly(4-vinyl pyridine) [2% crosslink] beads was washed several times with methanol, until the filtrate was colorless and then several times with toluene. The product was dried for 18 hours under vacuum.

B-HDI Trimerization Test

To 1 gm of the above resin was added 15 gm HDI. The mixture was stirred and heated at 125° C. for 7 hours. An IR spectrum of the liquid showed that 7% of the HDI had been converted to trimer.

C-TDI Trimerization Test

To 1 gm of the above resin was added 15 gm TDI. The mixture was stirred and heated at 115° C. for 4 hours. An IR spectrum of the liquid showed that less than 5% of the TDI had been converted to trimer.

D-TDI Trimerization Test with Propylene Oxide Added

To 1 gm of the above resin was added 15 gm TDI and 0.1 gm PO. The mixture was stirred and slowly heated to 85° C. over a period of 2 hours and then heated at 125° C. for 2 hours. An IR spectrum of the liquid showed that more than 30% of the TDI had been converted to trimer.

EXAMPLE 7

A-Preparation of a Polymer Bound 3,3'-bis(dimethylamino)-dipropyl methylamine Derived Catalyst To 25 gm Merrifield Resin [poly(styrene-co-vinylbenzyl- chloride), 1 meq Cl/gm, 1% crosslink] was added 500 ml toluene and 25 gm 3,3'-bis(dimethylamino)-dipropyl methylamine. The mixture was stirred and heated at 110° C. for 18 hours. The resin was isolated by filtration and washed several times with toluene. After drying for 18 hours under vacuum, 28.9 gm of a friable, pale yellow solid was recovered. Elemental analysis showed that the product was 1.9% nitrogen.

B-Trimerization Test

To 1 gm of the above resin was added 15 gm HDI. The mixture was stirred and slowly heated to 110° C. over a period of 3 hours and then heated at 135° C. for 3.5 hours. An IR spectrum of the liquid showed that less than 5% of the HDI had been converted to trimer.

C-Trimerization Test with Methanol Added

To 1 gm of the above resin was added 15 gm HDI and 0.1 gm methanol. The mixture was stirred and heated at 125° C. for 7 hours. An IR spectrum of the liquid showed that more than 20% of the HDI had been converted to trimer.

EXAMPLE 8

A-Preparation of a Polymer Bound 1,6-bis(dimethylamino)-hexane Derived Catalyst

To 25 gm Merrifield Resin [poly(styrene-co-vinylbenzyl- chloride), 1 meq Cl/gm, 1% crosslink] was added 500 ml toluene and 25 gm 1,6-bis(dimethylamino)-hexane. The mixture was stirred and heated at 80° C. for 18 hours. The resin was isolated by filtration and washed several times with toluene. After drying for 18 hours under vacuum, 29.0 gm of a white powder was recovered. Elemental analysis showed that the product was 1.45 nitrogen.

B-Trimerization Test

To 1 gm of the above resin was added 15 gm HDI. The mixture was stirred and heated at 130° C. for 3 hours. An IR spectrum of the liquid showed that less than 5% of the HDI had been converted to trimer. Methanol, 0.1 gm, was added to the mixture and the stirring and heating at 130° C. was continued for an additional 5 hours. An IR spectrum of the liquid showed that more than 20% of the HDI had been converted to trimer.

EXAMPLE 9

A-Preparation of a Polymer Bound Trimethyl-hydroxyethyl-ethylenediamine Derived Catalyst To 25 gm Merrifield Resin [poly(styrene-covinylbenzylchloride), 1 meq Cl/gm, 1% crosslink] was added 500 ml toluene and 21 gm trimethyl-hydroxyethylethylenediamine. The mixture was stirred and heated at 65° C. for 10 hours. The resin was isolated by filtration and washed several times with toluene, then several times with methanol, and then several times with water. After drying for 18 hours at 25° C. 8.6 gm was dried under vacuum at 40° C. to give a white solid.

B-Trimerization Test

To 1.05 gm of the above resin was added 112.2 gm HDI. The mixture was stirred and heated to 95°-100° C. for 4 hours. An IR spectrum of the liquid showed that 35% of the HDI had been converted to trimer.

EXAMPLE 10

A-Preparation of a Brominated Polystyrene

To 50 gm 200-400 mesh, 1% divinylbenzene crosslinked, polystyrene beads in 500 ml carbon tetrachloride in a 1000 ml flask covered with Al foil to protect from light, was added thallic acetate, 1.5 gm, followed by bromine, 8.0 gm in 20 ml of carbon tetrachloride. After 1.0 hr at 25° C. the mixture was refluxed for 1.0 hr. At the end of the reflux period there was no bromine color present. After cooling to 25° C. the mixture was filtered and the filtrate washed with carbon tetrachloride, 200 ml; methanol, 200 ml; methylene chloride, 200 ml; acetone, 200 ml; methylene chloride, 200 ml; and finally with methanol, 200 ml. The pale yellow solid was dried 18 hr in vacuo at 25° C. Elemental analysis gave 8.27% Br (1.0 meq Br/gm).

B-Preparation of Polymer Bound Arsine Oxide

To a mixture of the bromopolystyrene from above, 15.0 gm in 200 ml tetrahydrofuran, was added triphenylarsine, 3.25 gm, and lithium wire, 0.25 gm, cut into small pieces. After 2.5 hr reflux, bromobenzene, 0.5 ml, and bromine, 0.1 ml, was added. After 18 hr at 25° C. most of the lithium was consumed. The mixture was refluxed for 3 hr, cooled, filtered, the excess lithium removed, and washed with 500 ml of methanol followed by 250 ml of acetone. The light tan solid was suspended in 100 ml of acetone and 30% hydrogen peroxide, 6.0 gm, was added. After 18 hr at 25° C. the mixture was filtered, washed with 200 ml each of acetone and methanol. After drying in vacuo at 25° C., 14.7 gm of light yellow beads were obtained.

C-Trimerization Test

To 1.03 gm of the resin from B was added 130.8 gm HDI. The mixture was stirred and heated to 95°-100° C. for 3 hours. An IR spectrum of the liquid showed that 33.5% of the HDI had been converted to trimer.

While the invention has been described above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

Having thus described the invention, what is claimed is:

1. A process for preparing a trimer by cyclotrimerizing an isocyanate in a reaction medium in the presence of a polymer-bound trimerization catalyst to form an isocyanurate-containing cyclotrimerized isocyanate, said catalyst consisting essentially of a polymer backbone plus functional groups and said catalyst having a crosslink density of between 1% and 10%, and said catalyst having between 0.01 and 10 miliequivalent of catalytic sites per gram of said polymer, and said polymer being essentially insoluble in said reaction medium.

2. The process of claim 1 wherein said polymer-bound trimerization catalyst consists essentially of a polymer backbone plus functional groups, wherein said polymer backbone consists essentially of ethylene, propylene, isoprene, styrene, acrylate, and methacrylate moieties, and combinations thereof, and wherein said functional groups consist essentially of polymer bound derivatives of the following: aliphatic tertiary amines; aliphatic quaternary ammonium hydroxides and fluorides; quaternary ammonium, alkali and alkali metal salts of carboxylic acids and alcohols; organo-silyl amines, organo-phosphorous and organo-arsenic sites; and combinations thereof.

3. The process of claim 1 wherein said polymer-bound trimerization catalyst comprises nitrogen containing or arsine oxide containing functional groups, or a combination thereof.

4. The process of claim 1 wherein said polymer-bound trimerization catalyst comprises a tertiary amine.

5. The process of claim 1 wherein said polymer-bound trimerization catalyst has a crosslink density of between 1% and 5%.

6. The process of claim 1 wherein said polymer-bound trimerization catalyst is employed in an amount of between 0.01 and 10 parts of catalyst per 100 parts of said isocyanate.

7. The process of claim 1 wherein said cyclotrimerizing is effected in the presence of a co-catalyst employed in an amount of between about 1:1 and about 10:1 molar equivalents based upon the amount of polymer-bound catalyst employed.

8. A process for preparing a trimer by the steps of:
(a) cyclotrimerizing a polyisocyanate in the presence an essentially insoluble polymer-bound trimerization catalyst by contacting said polyisocyanate with said catalyst at a temperature of between about 20° and about 135° C. in a reaction to form an isocyanurate-containing cyclotrimerized isocyanate wherein a portion of the isocyanate moieties comprising said polyisocyanate are converted to isocyanurate groups, and
(b) separating said catalyst from said cyclotrimerized isocyanate in order to stop said reaction after a desired amount of isocyanate moieties in said polyisocyanate have been converted to isocyanurate moieties.

9. The process of claim 8 wherein said polymer-bound trimerization catalyst consists essentially of a polymer backbone plus functional groups, wherein said polymer backbone consists essentially of ethylene, propylene, isoprene, styrene, acrylate, and methacrylate moieties, and combinations thereof, and wherein said functional groups consist essentially of polymer bound derivatives of the following: aliphatic tertiary amines; aliphatic quaternary ammonium hydroxides and fluorides; quaternary ammonium, alkali and alkali metal salts of carboxylic acids and alcohols; organo-silyl amines, organo-phosphorous and organo-arsenic sites; and combinations thereof.

10. The process of claim 8 wherein said polymer-bound trimerization catalyst comprises nitrogen containing or arsine oxide containing functional groups, or a combination thereof.

11. The process of claim 8 wherein said polymer-bound trimerization catalyst comprises a tertiary amine.

12. The process of claim 8 wherein said polymer-bound trimerization catalyst has a crosslink density of between 1% and 10%.

13. The process of claim 8 wherein said polymer-bound trimerization catalyst has a crosslink density of between 1% and 5%.

14. The process of claim 8 wherein said polymer-bound trimerization catalyst a number of functional groups in an amount of between about 0.01 and about 10 milliequivalents of catalytic sites per gram of polymer.

15. The process of claim 8 wherein said polymer-bound trimerization catalyst is employed in an amount of between 0.01 and 10 parts of catalyst per 100 parts of said isocyanate.

16. The process of claim 8 wherein said cyclotrimerizing is effected in the presence of a co-catalyst being a primary or secondary alcohol employed in an amount of between about 1:1 and about 10:1 molar equivalents based upon the amount of polymer-bound catalyst employed.

17. A process for preparing a trimer by cyclotrimerizing an isocyanate in the presence a polymer-bound trimerization catalyst to form an isocyanurate-containing cyclotrimerized isocyanate wherein the polymer-bound trimerization catalyst consists essentially of a polymer having an alkyene group-containing polymer backbone and having trimerization catalyst moieties chemically bound to said polymer, said catalyst moieties being selected from the group consisting of: aliphatic tertiary amines; aliphatic quaternary ammonium hydroxides and fluorides; quaternary ammonium, alkali and alkali metal salts of carboxylic acids and alcohols; organo-silyl amines; organo-phosphorous and organo-arsenic compounds; and combinations thereof.

18. The process of claim 17 wherein said alkene group is selected from the group consisting of ethylene, propylene, isoprene, styrene, acrylates, methacrylates, and combinations thereof.

* * * * *